United States Patent [19]
Graham et al.

[11] Patent Number: 5,767,213
[45] Date of Patent: Jun. 16, 1998

[54] DIRECT APPLICATION OF SURFACE TREATMENT TO ABSORBENT POLYMERS

[75] Inventors: Andrew T. Graham, Midland; Don L. Stevens, Sanford, both of Mich.

[73] Assignee: The Dow Chemical Company, Midland, Mich.

[21] Appl. No.: 891,376

[22] Filed: May 29, 1992

[51] Int. Cl.$^6$ ..................................................... C08F 6/14
[52] U.S. Cl. ........................ 526/230; 528/494; 528/415; 528/496; 526/318.43
[58] Field of Search .............................................. 526/230

[56] References Cited

U.S. PATENT DOCUMENTS

| | | | |
|---|---|---|---|
| 4,286,082 | 8/1981 | Tsubakimoto et al. | 526/240 |
| 4,459,396 | 7/1984 | Yamasaki et al. | 526/200 |
| 4,708,997 | 11/1987 | Stanley, Jr. et al. | 526/207 |
| 4,898,913 | 2/1990 | Ziemelis et al. | 525/301 |
| 4,997,911 | 3/1991 | Yasui et al. | 528/495 |

FOREIGN PATENT DOCUMENTS

| | | |
|---|---|---|
| 0393692 | 10/1990 | European Pat. Off. |
| 9207336 | 8/1992 | WIPO |
| 9216565 | 10/1992 | WIPO |

OTHER PUBLICATIONS

U.S. application No. 07/671616, Stanley, Jr. et al., filed Mar. 19, 1991.

*Primary Examiner*—Joseph L. Schofer

[57] ABSTRACT

The subject invention pertains to a process for preparing a fluid absorbent polymer wherein an ethylenically unsaturated monomer mixture is dispersed as droplets in an inert organic phase containing a hydrophobic suspending agent, such droplets being polymerized to form polymer particles having a hydrophobic surface, the improvement comprising blending the polymer particles with a hydrophilic material in the absence of an organic solvent, such as to render the hydrophobic surface hydrophilic.

11 Claims, No Drawings

DIRECT APPLICATION OF SURFACE TREATMENT TO ABSORBENT POLYMERS

FIELD OF INVENTION

The present invention relates to absorbents formed of water insoluble, hydrogel-forming, polymeric materials that are capable of absorbing many times their own weight upon contact with aqueous fluids. More particularly, the present invention relates to a process for preparing such absorbents.

BACKGROUND OF INVENTION

Many water-insoluble hydrogel-forming polymers are useful as absorbents, due to their ability to imbibe and bind or immobilize aqueous fluids. These polymeric materials find employment in industry for various dewatering and fluid immobilization uses, such as water retaining agents in agricultural/horticultural fields, dehydration of oil, and like purposes. In recent years absorbent polymers having large capacities for absorbing aqueous fluids have been developed and have found use in personal care products for absorbing aqueous biological fluids. In a typical personal care product, such as a diaper, the aqueous fluid absorbent polymer is utilized in powder form, and is often mixed with cellulosic fibers that help initially absorb and distribute the fluid load. The polymeric materials of interest in such products are based upon a variety of polymers, including those derived from water soluble ethylenically unsaturated monomers or graft polymers in which unsaturated monomers are graft polymerized onto a polysaccharide (such as starch or cellulose) or other polymeric backbone.

A preferred absorbent material is derived from a water insoluble gel formed by copolymerizing an ethylenically unsaturated carboxylic acid with a multifunctional crosslinking monomer. The acid monomer or polymer is substantially neutralized with an alkali metal hydroxide, dried and pulverized into a powder form, before use in a personal care product. A preferred polymer gel is a copolymer of acrylic acid/sodium acrylate and any of a variety of crosslinkers.

Achieving desired polymeric characteristics that provide superior performance in a personal care product has long been a challenging goal of researchers. The product must perform for the user but also must be capable of being economically and safely made. At the customer/user level, a diaper, for example, should have a fast rate of absorption, adequate to imbibe and hold the fluid during absorption without leakage of fluid from the device in which it is employed. It is adequate fast rate, while maintaining all of the other desired qualities of the aqueous absorbent, that has often eluded prior researchers.

Water-in-oil suspension polymerization processes usefully provide such polymers. See U.S. Pat. Nos. 4,340,706, 4,367,323, and 4,446,261, the relevant portions herein incorporated by reference. In such processes, the aqueous monomer solution is dispersed as droplets in an organic oil phase. Such droplets are individually polymerized to form discrete polymer particles. Suspension polymerization processes provide several advantages in the preparation of water-swellable polymers. For instance, the reaction temperature and rate of reaction can be controlled, due to the heat transfer properties attendant in such polymerization processes. For example, the reaction temperature can be controlled by means of ebullient cooling. In addition, the polymer product so provided can be separated from the oil phase using such relatively efficient techniques as filtration or centrifugation.

U.S. Pat. No. 4,708,997, the relevant portions of which are incorporated herein by reference, discloses an improved suspension polymerization process wherein a suspending agent comprising hydrophobic fumed silicon dioxide and a copolymer of acrylic acid and lauryl methacrylate is provided in the oil phase. The use of such a suspending agent results in water-swellable polymer products of controlled particle size. However, the use of such a suspending agent imparts a hydrophobic surface to the polymer particles. Such a hydrophobic surface impedes the rate of aqueous fluid absorption.

U.S. patent application Ser. No. 761,616, the relevant portions of which are herein incorporated by reference, discloses a preferred suspension polymerization process, wherein the polymerization initiator is partially soluble in the oil phase. The use of such an initiator package causes crosslinking in the vicinity of the surface of the monomer droplet, which leads to high surface area polymer particles having convoluted and wrinkled surfaces. The process optionally incorporates the suspending agent set forth in U.S. Pat. No. 4,708,997.

U.S. Pat. No. 4,459,396 discloses the application of a hydrophilic material to the surface of a polymer particle by adding a water solution or dispersion of the hydrophilic material to the polymer while it is still suspended in the oil. This method incurs added expense in the removal of the extra water necessary to dissolve or disperse the hydrophilic material. Furthermore, the addition of extra dispersing phase to the polymerization system reduces the amount of material that can be initially polymerized in the vessel. Thus, batch size may be decreased, causing an undesirable increase in the cost of manufacture of the product.

U.S. patent application Ser. No. 761,616 discloses dissolving a hydrophilic material in methanol, applying the methanol/hydrophilic material solution to the polymer particles, and evaporating the methanol, typically at reduced pressure. This method has the disadvantage of using expensive solvents, and then either disposing of them or recycling them. Given their expense, production methods avoiding the need for solvent recycling will be preferred for industrial practice.

Those in industry would find great advantage in a suspension polymerization process wherein the particle size of the resultant polymer is controlled, but wherein rate of fluid absorption is not sacrificed. Such a process should not require significant processing steps, which add to production costs, and should minimize the use of organic solvents.

SUMMARY OF INVENTION

Accordingly, the subject invention provides a process for preparing a fluid absorbent polymer wherein an ethylenically unsaturated monomer mixture is dispersed as droplets in an inert organic phase containing a hydrophobic suspending agent, such droplets being polymerized to form polymer particles having a hydrophobic surface, the improvement comprising isolating the polymer particles from the organic phase and blending the polymer particles with a hydrophilic treatment such as to render the hydrophobic surface hydrophilic.

This and other embodiments are more fully discussed in the following detailed description.

DETAILED DESCRIPTION

The water absorbent compositions of the invention may be made from a variety of polymers or copolymers. Basically, any water-soluble ethylenically unsaturated monomer or mixture thereof that crosslinks to form a substantially water insoluble gel or particle is suitable. Crosslinked structures may be obtained by the copolymerization of a water-soluble monomer and a crosslinking monomer possessing at least two polymerizable double bonds in a molecular unit, as is well-known in the art. Monomer mixtures that include graft, as well as addition polymerizing systems may likewise be employed.

Suitable water-soluble monomers include those that are at least water-miscible and that are preferably sufficiently water-soluble to form at least a 5 weight percent solution when dissolved in water, and readily undergo addition polymerization. Exemplary water-soluble monomers include ethylenically unsaturated amides such as acrylamide, methacrylamide, and fumaramide as well as their N-substituted derivatives. Ethylenically unsaturated carboxylic acids such as acrylic, methacrylic, and crotonic acids and their salts are preferred. Suitable polycarboxylic acids include maleic acid and fumaric acids and itaconic acid. Preferred ethylenically unsaturated carboxylic acid esters include hydroxyethylacrylate, hydroxyethylmethacrylate, and esters of acrylic and methacrylic acids with polyethylene oxide. Vinyl amines such as vinyl pyridine and vinyl morpholine, and diallyl amines are also useful. Other suitable monomers are well known to those skilled in the art as discussed in U.S. Pat. No. 4,708,997, the relevant portions incorporated herein by reference.

The ethylenically unsaturated monomer may be partially neutralized as set forth below. In such cases, the monomer mixture will further comprise the salt of the ethylenically unsaturated monomer. The monomer mixture may also include components that graft polymerize onto one or more other monomer additional monomers of the monomer mixture. Polysaccharides, such as starch and cellulose are examples of graft-polymerizable components. Particularly suitable is a graft-polymerizable polyvinyl alcohol.

The suspension polymerization of the present invention, when carboxylic acid monomers are employed, generally provides that the monomers be neutralized at least partially prior to the polymerization. Preferably, the monomers will be neutralized such that they partition substantially to the aqueous phase, rather than to the oil phase. Preferably, the acid monomers will be between 50 and 95 percent neutralized, more preferably between 70 and 90 percent neutralized. The neutralization is generally carried out, as is well known in the art, by simply mixing the monomers, including any crosslinking agents, with any suitable base, e.g. an alkali hydroxide such as sodium hydroxide or potassium hydroxide or an alkali carbonate or bicarbonate such as sodium or potassium carbonate or bicarbonate, as the initial step of the process of preparation of the polymers of the invention. The neutralization is advantageously carried out at temperatures below 40° C., preferably below 35° C.

The monomer mixture typically includes one or more crosslinking monomers which comprise organic compounds having two or more ethylenic groups copolymerizable with the water-soluble monomers of the monomer mixture. The crosslinking agent may be incorporated into the aqueous phase, the oil phase, or both. The crosslinking agent can be employed in an amount sufficient to provide to the polymerization product a water-swellable character. Exemplary crosslinking monomers include diacrylate or dimethacrylate of ethylene glycol, diethylene glycol, triethylene glycol, tetraethylene glycol, propylene glycol, 1,4-butane diol, 1,5-pentane diol, 1,6-hexane diol, neopentyl glycol, trimethylol propane and pentaerythritol; triacrylates or trimethacrylates of trimethylol propane and pentaerythritol tetracrylates or tetramethacrylates of pentaerythritol, N,N'-methylene-bis-acrylamide; N,N'-methylene-bis-methacrylamide; allyl methacrylate; and triallyl isocyanurate. Other crosslinking monomers include polyhaloalkanols; sulfonium zwitterions; haloepoxyalkanes; polyglycidyl ethers; aminoepihalohydrin adducts; multivalent metal ions such as aluminum or calcium; glycidyl acrylates; and the like. Preferred crosslinkers include methylene-bis-acrylamide, trimethylol propanetriacrylate and diethylene glycol diacrylate and tetraethylene glycol diacrylate. Crosslinking monomers are present in the dispersion of water-soluble monomer in an amount effective to crosslink the water-soluble polymer. Typically, the crosslinking monomer is used in amounts ranging from about 0.0001 to about 5 parts by weight, more preferably from about 0.01 to about 1 parts by weight, based on 100 parts by weight of the water-soluble monomer used.

In the suspension polymerization process of the invention, the monomer mixture is suspended in an inert organic phase or oil phase comprising an organic material that is non-reactive with the monomers and resulting products. The water-immiscible oil phase of the suspension generally comprises as least one inert hydrophobic liquid, such as a liquid hydrocarbon or substituted liquid hydrocarbon. Preferred organic liquids are the halogenated hydrocarbons such as perchloroethylene, methylene chloride, and liquid hydrocarbons having 4 to 15 carbon atoms per molecule, including aromatic and aliphatic hydrocarbons and mixtures thereof such as benzene, xylene, toluene, mineral oils, liquid paraffins such as kerosene, and naphtha. Of the foregoing organic liquids, the hydrocarbons are the more preferred, with the aliphatic hydrocarbons being most preferred. A preferred commercially available aliphatic hydrocarbon is ISOPAR® M deodorized kerosene, sold by Exxon.

The inert organic or oil phase includes dispersing agents to keep the aqueous soluble monomer droplets suspended in an oil phase for the suspension polymerization. These dispersing agents include surface active materials such as sucrose fatty acid esters and/or polyglycerol fatty acid esters. Also included are nonionic surface active agents having HLB values of from 2 to 6. Polymeric materials useful as dispersants include the various cellulose ethers, such as ethyl cellulose, methyl cellulose, hydroxyethyl cellulose, hydroxypropyl cellulose, carboxyethyl cellulose and combinations thereof. Preferably, such cellulose ethers will be provided at a concentration of from 0.1 to 2 weight percent, based on the weight of the monomer, more preferably 0.5 weight percent based on the weight of the monomer. Other useful materials include the hydrophobic clays such as cationic surfactant treated bentonite clays. The preferred dispersing agent, set forth in U.S. Pat. No. 4,708,997, is a mixture of a fumed hydrophobic silica (such as AEROSIL™ R-972 fumed silica manufactured by Degussa, Inc.) and a copolymer of lauryl methacrylate and acrylic acid. In a preferred copolymer, the mole ratio of lauryl methacrylate to acrylic acid in the copolymer is 99 to 1.

In general, an aqueous phase containing water-soluble monomer(s) typically is dispersed in the inert hydrophobic liquid which optionally contains a suspending agent. Typically, is is desirable to agitate the resulting composition. Factors such as the rate of agitation of the composition control properties such as the droplet or particle size of the suspended aqueous phase.

The suspension polymerization processes are performed by following the general procedures described in the art as exemplified in U.S. Pat. Nos. 4,340,706, 4,367,323, 4,446,261, and 4,708,997 and U.S. patent application Ser. No. 671,616, the relevant portions of these references incorporated herein by reference. Normally, such polymerization is practiced in the presence of a polymerization initiator capable of generating free-radicals. Preferably, the free-radical initiator is employed in amounts from about 0.01 to about 0.1 weight percent of initiator based on the monomers. Exemplary polymerization initiators include the inorganic persulfates such as potassium persulfate, ammonium persulfate and sodium persulfate; azo catalysts such as azobisisobutyronitrile and dimethylazoisobutyrate; organic peroxygen compounds such as benzoyl peroxide, t-butylperoxide, isopropylbenzene hydroperoxide (cumene hydroperoxide), t-butyl hydroperoxide, and compounds such as sodium borohydride. Of these initiators, the organic types such as t-butyl hydroperoxide are preferred. In addition to the aforementioned ingredients, the suspension polymerization recipe optionally includes chain transfer agents, chelating agents, buffers, salts, and the like.

In one particular embodiment, the polymerization of the monomer droplets suspended in the oil phase will be initiated in the oil phase by means of an initiator that is at least partially oil phase soluble. Preferably, the reducing agent will partition such as to provide between 10 and 2500 ppm reducing agent in the oil phase, more preferably at least 100 ppm reducing agent in the oil phase. A preferred reducing component of the redox system is sulfur dioxide gas. In particular, the preferred redox package will include t-butyl hydroperoxide and sulfur dioxide. In this case, the reaction is initiated by bubbling the sulfur dioxide into the reaction mixture. Further details are set forth in U.S. patent application Ser. No. 671,616, the relevant portions herein incorporated by reference.

After the polymerization reaction is finished, the polymer product is recovered by removing the inert oil phase and drying. Preferably, the polymer product will be dried to a water content less than about 30 weight percent, more preferably less than about 8 weight percent, based on the weight of the polymer product.

The dried, finished product may then be treated with a wetting agent, such as VORANOL® 2070 polyol, manufactured by The Dow Chemical Company. The wetting agent helps overcome the adverse effect of any remaining dispersing agent, such as hydrophobic inert inorganic silica material, remaining on the finished product. The wetting agent serves to render the polymers hydrophilic on their surfaces. The utilization of the wetting agent serves to improve the rate of absorbency of the polymer, i.e., it decreases the vortex rate and the swell time.

The desired amount of wetting agent may be determined empirically, bearing in mind that in industrial practice it is desirable to minimize the amount of additive for economic reasons. Preferably, the dry polymer beads will be mixed with 0.1 to 2.5 weight percent wetting agent based on the weight of the dry beads, more preferably 0.3 to 1.5 weight percent. More preferably, 0.5 to 1 weight percent wetting agent based on the weight of dry polymer will be provided.

The rate at which the polymers of interest will absorb aqueous fluid is a key advantage of the invention. In particular, "Vortex Rate" is measured by weighing 50 grams of a 0.9 percent aqueous sodium chloride solution into a 100 mL beaker. The beaker is placed on a magnetic stirrer such that there is a substantial vortex. To the side of the vortex is added 2 grams of the material to be tested. The time is started when all the material has been added; the time is stopped when the vortex disappears.

The "Swell Rate" of the polymer is determined by the following procedure. Twenty (20) grams of a 0.9 percent aqueous sodium chloride solution is weighed into a small beaker. One (1) gram of the material to be tested is weighed into a large weigh boat (about 5 cm in diameter). The absorbent resin powder is spread uniformly over the bottom of the weigh boat. The sodium chloride solution is added and a timer is started. The timer is stopped when there is no longer any free liquid remaining.

Suitable hydrophilic materials include VORANOL polyols such as VORANOL 2070, VORANOL 2100, and VORANOL 3100 (all available from The Dow Chemical Company), TRITON X-100 surfactant (available from Rohm and Haas), TERGITOL 15-S-9 ethoxylated surfactant (available from Union Carbide), polyethylene glycols, and nonionic surfactants having an HLB value of at least 7. Although it is not necessary to include water or solvents in the addition of the hydrophilic treatment to the dry polymer powder, amounts of water up to 20 times the amount of the hydrophilic treatment may be employed.

The hydrophilic treatment should be thoroughly mixed with the polymer particles, i.e., sufficient blending time should be allowed for all of the particles to come in contact with one another, and thus spread the surface treatment uniformly over the surfaces of all the particles. The length of time required for adequate blending is a function of the equipment used to perform the blending; determination of a preferred blending time for the particular system employed may be readily determined by one having skill in the art. Examples of blending equipment/processes include simple tumbling of a jar, or blending in a conical dryer, ribbon blender, drum tumbler, etc.

The polymers of the invention may be utilized as a principal absorbing component of a personal care product. A typical product is a disposable diaper wherein the polymer of the invention is contained in a composite structure generally comprising an exterior impervious sheet and a porous interior sheet, with the polymer of the invention, typically mixed with cellulose fibers, sandwiched between said sheets.

Other absorbent structures into which the polymers of the invention may be utilized include incontinence devices, sanitary napkins, paper towels, and facial tissues.

The following examples are provided for the purpose of illustration, rather than limitation. All parts and percentages are given by weight, unless otherwise indicated.

EXAMPLE ONE

One hundred ninety-two (192) pounds of acrylic acid, 702 grams of diethylene glycol diacrylate, 348 grams of VERSENEX 80 chelating agent (available from The Dow Chemical Company), and 330 pounds of water were added to a vessel. After agitation, 192 pounds of a 50 weight percent aqueous solution of sodium hydroxide were added to partially neutralize the acrylic acid. Nine hundred eighty (980) pounds of a high isoparaffinic content hydrocarbon solvent (IBP=188° C., specific gravity=0.767) were added to a second vessel. Seven hundred twenty-six (726) grams of a lauryl methacrylate copolymer with acrylic acid, 454 grams of AEROSIL R972 hydrophobic surface treated silicon dioxide (available from Degussa, Inc.), and 50 pounds of the same hydrocarbon solvent were added to a third vessel. Forty-six (46) grams of sodium persulfate in an aqueous solution were added to the first vessel. The contents of the third vessel, and then the contents of the first vessel, were added to the second vessel with agitation. Two hundred seventy (270) grams of a 70% aqueous solution of t-butyl hydroperoxide and 892 grams of trimethyol propane triacrylate were added. A 1% solution of sulfur dioxide in nitrogen was added to the bottom of the vessel at the rate of 0.7 SCFM (14 liters/minute), and the reaction was allowed to proceed.

Three batches of polymer made in accordance with this procedure were blended to give polymer A.

Samples of polymer A were post-treated with hydrophilic treatements according to the process of the subject invention to yield absorbent resin powders B, C, D, E, G, H, and I. To prepare each sample, 100 grams of polymer A were weighed into a container. A pre-weighed amount of hydrophilic treatment was added to the sample using a syringe. This was accomplished by successively adding powdered absorbent resin and hydrophilic treatment in proportion to a 16 ounce jar and swirling the powder in the jar after each successive addition. When all of the powder and the treatment were added to the jar, the jar was capped and inverted by hand from 20 to 30 times to help mix the materials. The jar was then placed on a roll mixer for 15 minutes.

Comparative resin F was made by treating polymer A according to the following procedure. Fifty (50) grams of polymer A were weighed into a round bottom flask. Into this flask enough methanol was poured so that the liquid level was about 1 cm above the level of the resin. Then, 0.5 grams of VORANOL 2070 polyol was weighed into the flask. The flask was placed in an 85° C. water bath and was subjected to vacuum to remove the methanol. The polymer F was removed and tested as described below.

Polymers A through I were tested for Vortex Rate and Swell Time, with the results shown in Table One below. The hydrophilic treatment used and the weight percent of such hydrophilic treatment are set forth in Table One.

TABLE ONE

| Polymer | Hydorphilic Treatment | Wt. % Hydrophilic Treatment | Vortex Rate (sec) | Swell Time (sec) |
|---|---|---|---|---|
| A | none | — | 32.8 | 59.0 |
| B | VORANOL 2070 | 0.5 | 14.3 | 17.7 |
| C | VORANOL 2070 | 1.0 | 14.5 | 16.8 |
| D | VORANOL 2070 | 1.5 | 14.8 | 17.0 |
| E | VORANOL 3100 | 1.0 | 14.1 | 17.1 |
| G | VORANOL 2100 | 1.0 | 15.4 | 22.0 |
| H | TRITON X-100 | 1.0 | 14.7 | 17.3 |
| I | TERGITOL 15-S-9 | 1.5 | 15.0 | 16.6 |
| Compartive Resin F | VORANOL 2070 | 1.0 | 14.9 | 17.9 |

As the above data indicates, the process of the subject invention produces polymers with comparable Vortex Rates and Swelling Times, as compared to those produced by the prior art process described in the preparation of Polymer F, and improved Vortex Rates and Swelling Times, as compared with untreated material of Sample A.

EXAMPLE TWO

One thousand fifty (1050) pounds of polymer J were prepared by the procedure set forth in Example One for the preparation of polymer A, and were weighed into a conical vacuum dryer whose agitation was provided by a revolving, rotating screw. While the agitator was running, 10.5 pounds of VORANOL 2070 polyol were added. Mixing was continued for two to three hours, until the polymer and the hydrophilic surface treatment were fully mixed. Sample K was drawn for analysis, with the results set forth in Table Two.

TABLE TWO

| Polymer | Hydrophilic Treatment | Wt. % Hydrophilic Treatment | Vortex Rate (sec) | Swell Time (sec) |
|---|---|---|---|---|
| J | none | — | 35.8 | 68.3 |
| K | VORANOL 2070 | 1.0 | 15.0 | 17.6 |

EXAMPLE THREE

A polymer was made by the procedure set forth in Example One for the preparation of polymer A. Fifty (50) gram samples of the polymer were treated with the treatment solutions shown in Table Three below, with the Vortex Rate of the resultant polymers likewise presented. Mixing of the surface treatment with the polymer was accomplished as in Example One.

TABLE THREE

| Polymer | Water (gms) | Voranol 2070 Polyol (gms) | Voranol 2070 Polyol (wt %) | Vortex Rate |
|---|---|---|---|---|
| L | 0.0 | 0.625 | 1.25 | 24 |
| M | 19.25 | 0.375 | 0.75 | 23 |
| N | 19.0 | 0.50 | 1.00 | 24 |
| O | 18.75 | 0.625 | 1.25 | 25 |
| P | 18.5 | 075 | 1.50 | 25 |

What is claimed is:

1. In a process for preparing a fluid absorbent polymer wherein an ethylenically unsaturated monomer mixture is dispersed as droplets in an inert organic phase containing a hydrophobic suspending agent, such droplets being polymerized to form polymer particles whereupon a portion of the hydrophobic suspending agent remains on the surface of the polymer rendering the polymer surface hydrophobic, the improvement comprising isolating the polymer particles from the organic phase and coating the polymer particles with a hydrophilic material in the absence of an organic solvent, such as to render the polymer surface hydrophilic.

2. The process of claim 1, wherein the hydrophilic material is a polyol, a polyethylene glycol, or a nonionic surfactant having an HLB value of at least 7.

3. The process of claim 1, wherein the hydrophilic material is provided at a level of about 0.1 to about 2.5 weight percent, based on the weight of the polymer particles.

4. The process of claim 1, wherein the hydrophilic material is provided at a level of about 0.3 to about 1.5 weight percent, based on the weight of the polymer particles.

5. The process of claim 1, wherein the ethylenically unsaturated monomer mixture comprises a monomer selected from the group consisting of acrylic acid, methacrylic acid, and salts thereof.

6. The process of claim 1, wherein the hydrophobic suspending agent comprises hydrophobic fumed silicon dioxide and a copolymer of acrylic acid and lauryl methacrylate.

7. The process of claim 1, wherein the droplets are polymerized in the presence of a crosslinking agent having two or more ethylenic groups copolymerizable with the monomer mixture.

8. The process of claim 7, wherein the crosslinking agent is trimethylol propane triacrylate, methylene-bis-acrylamide, diethyleneglycol diacrylate, tetraethyleneglycol diacrylate, or mixtures thereof.

9. The process of claim 1, wherein the droplets are polymerized in the presence of an initiator package comprising an oxidizing component and a reducing component.

10. The process of claim 9, wherein the oxidizing component is t-butyl hydroperoxide, cumene hydroperoxide, or 2,5-dihydroperoxy-2,5-dimethylhexane.

11. The process of claim 9, wherein the reducing component is sulfur dioxide.

* * * * *